United States Patent
Hwang et al.

(10) Patent No.: US 11,465,138 B2
(45) Date of Patent: Oct. 11, 2022

(54) METHOD FOR PRODUCING METAL COMPLEX CATALYST, AND METAL COMPLEX CATALYST PRODUCED BY SAME

(71) Applicant: LG Chem, LTD., Seoul (KR)

(72) Inventors: Sunhwan Hwang, Daejeon (KR); Kyong Yong Cha, Daejeon (KR); Dong Hyun Ko, Daejeon (KR); Ye Seul Hwang, Daejeon (KR); Jun Kyu Han, Daejeon (KR); Sang Jin Han, Daejeon (KR); Seongmin Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 177 days.

(21) Appl. No.: 16/965,586

(22) PCT Filed: Apr. 10, 2019

(86) PCT No.: PCT/KR2019/004251
§ 371 (c)(1),
(2) Date: Jul. 28, 2020

(87) PCT Pub. No.: WO2019/199042
PCT Pub. Date: Oct. 17, 2019

(65) Prior Publication Data
US 2021/0046469 A1    Feb. 18, 2021

(30) Foreign Application Priority Data

Apr. 10, 2018    (KR) .................. 10-2018-0041559

(51) Int. Cl.
*B01J 37/03*    (2006.01)
*B01J 23/80*    (2006.01)
(Continued)

(52) U.S. Cl.
CPC ............. *B01J 37/031* (2013.01); *B01J 23/80* (2013.01); *B01J 37/08* (2013.01); *C07C 5/48* (2013.01);
(Continued)

(58) Field of Classification Search
CPC ... B01J 37/01; B01J 23/80; B01J 37/08; B01J 2523/27; B01J 2523/842; C07C 5/48; C07C 11/167
(Continued)

(56) References Cited

U.S. PATENT DOCUMENTS 3,270,080 A  *  8/1966  Christmann ......... B01J 27/1853
                                                       585/622
3,420,911 A  *  1/1969  Karkalits, Jr. ............ C07C 5/42
                                                       585/443
(Continued)

FOREIGN PATENT DOCUMENTS

CN    105772045    7/2016
JP    46-005064    11/1971
(Continued)

OTHER PUBLICATIONS

Grasset, F. et al., "Synthesis and Magnetic Characterization of Zinc Ferrite Nanoparticles with Different Environments: Powder, Colloidal Solution, and Zinc Ferrite-Silica Core-Shell Nanoparticles," Langmuir (2002) 18 (21):8209-8216.
(Continued)

*Primary Examiner* — Patricia L. Hailey
(74) *Attorney, Agent, or Firm* — Dentons US LLP

(57) ABSTRACT

A method for preparing a metal complex catalyst by (A) obtaining a precipitate by bringing a metal precursor solution comprising a zinc (Zn) precursor, a ferrite (Fe) precursor, and water into contact with a basic aqueous solution; (B) obtaining a zinc ferrite catalyst by filtering and calcining the
(Continued)

precipitate; and (C) supporting an acid onto the zinc ferrite catalyst, and a metal complex catalyst prepared thereby.

12 Claims, 1 Drawing Sheet

(51) Int. Cl.
*B01J 37/08* (2006.01)
*C07C 5/48* (2006.01)
*C07C 11/167* (2006.01)

(52) U.S. Cl.
CPC ...... *B01J 2523/27* (2013.01); *B01J 2523/842* (2013.01); *C07C 11/167* (2013.01)

(58) Field of Classification Search
USPC ........ 502/329, 524; 423/594.1, 594.14, 621; 585/654
See application file for complete search history.

(56) References Cited

U.S. PATENT DOCUMENTS

| | | | | |
|---|---|---|---|---|
| 3,828,101 A | * | 8/1974 | Miklas | ..................... B01J 37/03 502/328 |
| 3,849,545 A | * | 11/1974 | Miklas | ................. B01J 37/0018 585/629 |
| 3,953,370 A | * | 4/1976 | Miklas | ..................... C07C 5/48 502/329 |
| 3,960,767 A | | 6/1976 | Christmann et al. | |
| 4,083,884 A | | 4/1978 | Purdy | |
| 4,658,074 A | * | 4/1987 | Bajars | ..................... C07C 5/48 585/443 |
| 2010/0121123 A1 | | 5/2010 | Chung et al. | |
| 2013/0217568 A1 | * | 8/2013 | Hazin | .................... B01J 23/002 502/226 |

FOREIGN PATENT DOCUMENTS

| | | |
|---|---|---|
| JP | 2010-534553 | 11/2010 |
| KR | 10-0847206 | 7/2008 |
| KR | 10-2011-0036290 | 4/2011 |
| KR | 10-2011-0130130 | 12/2011 |
| KR | 10-2014-0082869 | 7/2014 |

OTHER PUBLICATIONS

Chung et al., "Prevention of Catalyst Deactivation in the Oxidative Dehydrogenation of n-Butene to 1,3-Butadiene over Zn-Ferrite Catalysts," Catalysis Letters, published online May 21, 2009, pp. 579-586, vol. 131.
Park et al., "Oxidative Dehydrogenation of 1-butene over BiFe0. 65MoP0.1 Catalyst: Effect of Phosphorous Precursors," Korean Chem. Eng. Res., 2015, pp. 824-830, vol. 53, No. 6, in Korean with English Abstract.

* cited by examiner

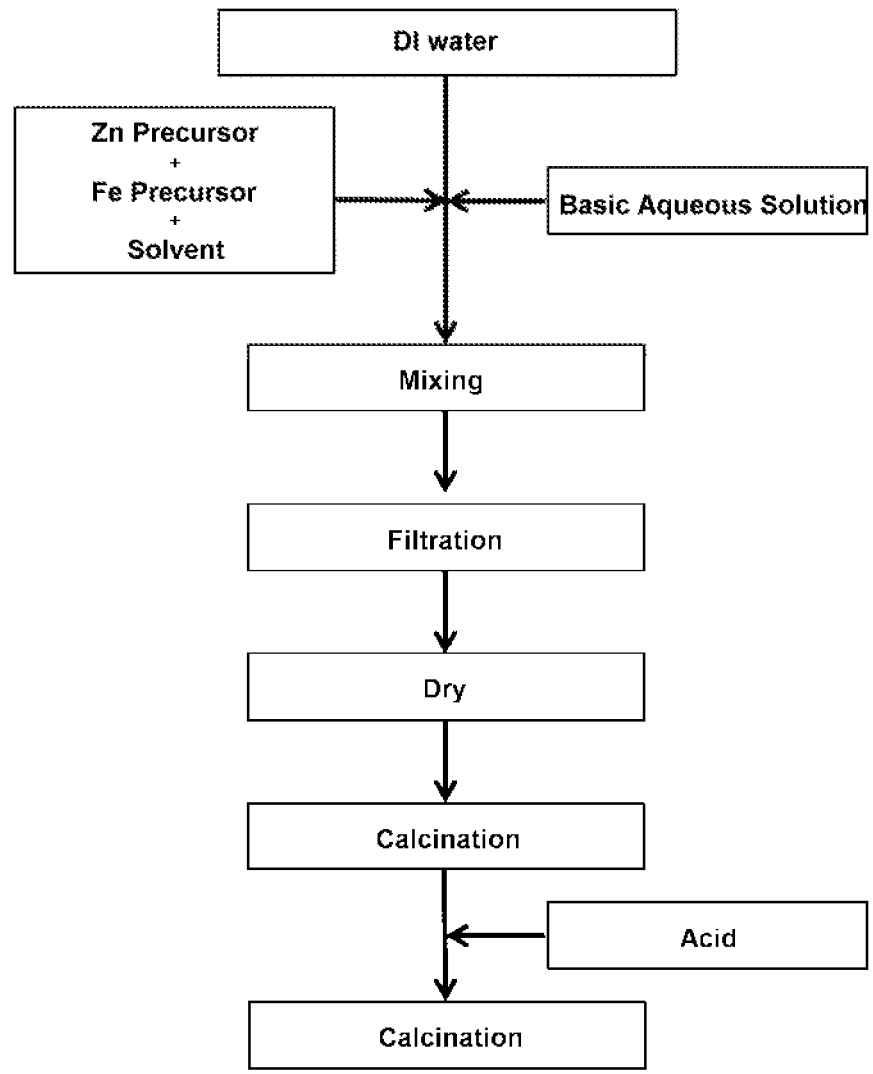

METHOD FOR PRODUCING METAL COMPLEX CATALYST, AND METAL COMPLEX CATALYST PRODUCED BY SAME

This application is a National Stage Application of International Application No. PCT/KR2019/004251 filed on Apr. 10, 2019, which claims priority to and the benefit of Korean Patent Application No. 10-2018-0041559 filed in the Korean Intellectual Property Office on Apr. 10, 2018, the entire contents of which are incorporated herein by reference.

TECHNICAL FIELD

The present specification relates to a method for preparing a metal complex catalyst and a metal complex catalyst prepared thereby.

BACKGROUND 1,3-butadiene is an intermediate of petroleum chemical products, and demands for 1,3-butadiene and the value thereof are gradually increasing globally. The 1,3-butadiene has been prepared by using naphtha cracking, the direct dehydrogenation reaction of butene, the oxidative dehydrogenation reaction of butene, and the like.

However, since the naphtha cracking process consumes a lot of energy due to high reaction temperature, and is not a single process for producing only 1,3-butadiene, there is a problem in that other fundamental fractions in addition to 1,3-butadiene are produced in excess. Further, the direct dehydrogenation reaction of n-butene is thermodynamically adverse and requires high temperature and low pressure conditions for producing 1,3-butadiene with high yield as an endothermic reaction, and thus is not suitable as a commercialization process for producing 1,3-butadiene.

Meanwhile, the oxidative dehydrogenation reaction of butene is a reaction in which butene and oxygen react with each other in the presence of a metal oxide catalyst to produce 1,3-butadiene and water, and has a very thermodynamically favorable advantage because stable water is produced. Further, since the oxidative dehydrogenation reaction of butene is an exothermic reaction unlike the direct dehydrogenation reaction of butene, 1,3-butadiene with high yield can be obtained even at lower reaction temperature than the direct dehydrogenation reaction, and the oxidative dehydrogenation reaction of butene can become an effective single production process capable of satisfying the demands for 1,3-butadiene because an additional heat supply is not required.

The metal oxide catalyst is generally synthesized by a precipitation method, and since the one-time amount of metal oxide catalyst produced is small due to technical and spatial limitations, the catalyst is prepared by repeating the same process several times in order to satisfy a target amount. The catalysts thus prepared over several times can have different reactivity with the reactant depending on the preparation order, and such a difference in reactivity among the catalysts is directly related to the yield of the product (butadiene), so that studies to reduce the difference in reactivity among the catalysts have been continuously carried out.

Technical Problem

The present specification provides a method for preparing a metal complex catalyst and a metal complex catalyst prepared thereby.

Technical Solution

An exemplary embodiment of the present specification provides a method for preparing a metal complex catalyst, the method comprising: (A) obtaining a precipitate by bringing a metal precursor solution comprising a zinc (Zn) precursor, a ferrite (Fe) precursor, and water into contact with a basic aqueous solution; (B) obtaining a zinc ferrite catalyst by filtering and calcining the precipitate; and (C) supporting an acid onto the zinc ferrite catalyst.

Further, an exemplary embodiment of the present specification provides a method for preparing butadiene, the method comprising: preparing butadiene by using the metal complex catalyst, prepared according to the above-described method for preparing a metal complex catalyst, in an oxidative dehydrogenation reaction of butene.

An exemplary embodiment of the present specification provides a metal complex catalyst comprising a zinc ferrite catalyst and an acid.

Advantageous Effects

The method for preparing a metal complex catalyst according to an exemplary embodiment of the present specification has effects of improving the conversion of butene and the selectivity of butadiene by supporting phosphoric acid onto a zinc ferrite catalyst to suppress a complete oxidation reaction which is a side reaction of an oxidative dehydrogenation reaction.

BRIEF DESCRIPTION OF THE DRAWINGS

FIG. 1 is a process diagram for performing a method for preparing a metal complex catalyst according to an exemplary embodiment of the present specification.

DETAILED DESCRIPTION

Hereinafter, the present specification will be described in more detail.

In the present specification, the 'yield (%)' is defined as a value obtained by dividing the weight of 1,3-butadiene as a product of an oxidative dehydrogenation reaction by the weight of butene (BE) as a raw material. For example, the yield can be represented by the following equation.

Yield (%)=[(the number of moles of 1,3-butadiene produced)/(the number of moles of butene supplied)]×100

In the present specification, the 'conversion (%)' refers to a rate at which a reactant is converted into a product, and for example, the conversion of butene can be defined by the following equation.

Conversion (%)=[(the number of moles of butene reacting)/(the number of moles of butene supplied)]×100

In the present specification, the 'selectivity (%)' is defined as a value obtained by dividing the change amount of butadiene by the change amount of butene. For example, the selectivity can be represented by the following equation.

Selectivity (%)=[(the number of moles of 1,3-butadiene or COx produced)/(the number of moles of butene reacting)]×100

In the present specification, the 'COx' means a compound comprising carbon monoxide (CO), carbon dioxide ($CO_2$), and the like, which is formed during an oxidative dehydrogenation reaction.

In the specification, the 'butadiene' means 1,3-butadiene.

An exemplary embodiment of the present specification provides a method for preparing a metal complex catalyst, the method comprising: (A) obtaining a precipitate by bringing a metal precursor solution comprising a zinc (Zn) precursor, a ferrite (Fe) precursor, and water into contact with a basic aqueous solution; (B) obtaining a zinc ferrite catalyst by filtering and calcining the precipitate; and (C) supporting an acid onto the zinc ferrite catalyst.

A zinc ferrite catalyst ($ZnFe_2O_4$) used in an oxidative dehydrogenation reaction is generally prepared by a co-precipitation method. Since a catalyst prepared by a co-precipitation method is prepared in a bulk form, an α-iron oxide (α-$Fe_2O_3$) phase is formed. The α-iron oxide (α-$Fe_2O_3$) phase acts as a cause to reduce the selectivity of 1,3-butadiene which is a product in an oxidative dehydrogenation reaction of butene.

Accordingly, the present inventors suppressed a complete oxidation reaction which is a side reaction of the oxidative dehydrogenation reaction of butene by supporting phosphoric acid onto a zinc ferrite catalyst prepared by a co-precipitation method. Six oxygens ($O_2$) are consumed during the complete oxidation, and when the complete oxidation reaction is suppressed, the conversion of butene and the selectivity of butadiene can be ultimately improved by reducing the consumption of oxygen which is supplied together with butene which is a reactant. Through this, it was possible to improve the reactivity of the zinc ferrite catalyst prepared by the co-precipitation method.

Further, when an acid is added in a process of extruding and molding a catalyst (Korean Patent Application Laid-Open No. 2014-0082869), the acid is added for the purpose of peptizing an inorganic binder, and in this case, the acid is not used in a reaction because the acid is not removed during a heat treatment process after the extrusion. However, when an acid is supported onto a catalyst as in the present invention, the catalyst is used as a supported catalyst in the oxidative dehydrogenation reaction, so that the purpose of using an acid is different from that in the aforementioned case.

According to an exemplary embodiment of the present specification, in Step (A), a content of the zinc precursor can be 0.1 wt % to 5 wt %, specifically, 0.1 wt % to 3 wt %, based on 100 wt % of water of the metal precursor solution.

According to an exemplary embodiment of the present specification, in Step (A), a content of the ferrite precursor can be 1 wt % to 10 wt %, specifically, 1 wt % to 7 wt %, based on 100 wt % of water of the metal precursor solution. When the contents of the zinc precursor and the ferrite precursor satisfy the above ranges, a metal complex catalyst is easily synthesized during the formation of a precipitate by the co-precipitation method.

According to an exemplary embodiment of the present specification, the acid in Step (C) can be phosphoric acid. Specifically, when a catalyst is prepared by supporting phosphoric acid onto a zinc ferrite catalyst prepared by the co-precipitation method, it is possible to suppress a complete oxidation reaction which is a side reaction during an oxidative dehydrogenation reaction of butene.

According to an exemplary embodiment of the present specification, a content of the acid based on 100 wt % of the zinc ferrite catalyst in Step (C) can be 0.05 wt % to 0.2 wt %, more specifically, 0.05 wt % to 0.1 wt %. When the content of the acid is less than 0.05 wt %, phosphoric acid is not sufficiently supported, so that the side reaction of the oxidative dehydrogenation reaction can not be sufficiently prevented, and when the content thereof is more than 0.2 wt %, the acid is supported excessively to suppress the activity of the catalyst, so that the conversion of butene and the selectivity of butadiene can be reduced.

According to an exemplary embodiment of the present specification, the zinc precursor and the ferrite precursor can be each independently one or more selected from the group consisting of a nitrate, an ammonium salt, a sulfate, and a chloride, or a hydrate thereof.

According to an exemplary embodiment of the present specification, the zinc precursor can be zinc chloride ($ZnCl_2$).

According to an exemplary embodiment of the present specification, the ferrite precursor can be ferric chloride hydrate ($FeCl_3 \cdot 6H_2O$).

According to an exemplary embodiment of the present specification, a pH of the basic aqueous solution can be 7 to 11. Specifically, a pH of the basic aqueous solution can be more than 7 and 11 or less. More specifically, a pH of the basic aqueous solution can be 8 to 11. When the pH of the basic aqueous solution satisfies the above range, there is an effect of stably producing a metal complex catalyst.

According to an exemplary embodiment of the present specification, the basic aqueous solution can be one or more selected from the group consisting of potassium hydroxide, ammonium carbonate, ammonium bicarbonate, an aqueous sodium hydroxide solution, an aqueous sodium carbonate solution, and ammonium water. Preferably, the basic aqueous solution can be ammonia water.

According to an exemplary embodiment of the present specification, a concentration of the basic aqueous solution can be 20 wt % to 40 wt %. Specifically, a concentration of the basic aqueous solution can be 25 wt % to 30 wt %.

According to an exemplary embodiment of the present specification, the obtaining of the precipitate can further comprise bringing the metal precursor solution into contact with the basic aqueous solution, and then stirring the resulting solution. The formation of precipitations of metal precursors is facilitated by further comprising the stirring of the resulting solution, so that catalyst particles are favorably formed.

According to an exemplary embodiment of the present specification, the stirring of the resulting solution can be performed at room temperature.

According to an exemplary embodiment of the present specification, a method for the stirring of the resulting solution can be used without limitation as long as the method mixes a liquid with a liquid.

According to an exemplary embodiment of the present specification, the stirring time in the stirring of the resulting mixture can be 30 minutes to 3 hours. Specifically, the stirring time is preferably 1 hour to 2 hours.

According to an exemplary embodiment of the present specification, the method can further comprise washing the precipitate before the precipitate is filtered and then calcined. Unnecessary ions remaining in the precipitate can be removed by further comprising the washing of the precipitate.

According to an exemplary embodiment of the present specification, the method can further comprise drying the precipitate before the precipitate is filtered and then calcined in Step (B).

According to an exemplary embodiment of the present specification, the drying of the precipitate can be performed before the precipitate is calcined after the precipitate is filtered and then washed.

According to an exemplary embodiment of the present specification, the drying of the precipitate can be performed at 80° C. to 150° C.

According to an exemplary embodiment of the present specification, the calcining of the precipitate can be increasing the temperature up to 650° C. at a rate of 1° C./min, and then calcining the precipitate for 6 hours. A method for the calcining of the precipitate can be a heat treatment method typically used in the art.

According to an exemplary embodiment of the present specification, the calcining of the precipitate can be performed by injecting the air at 1 L/min into a calcining furnace.

According to an exemplary embodiment of the present specification, the method can further comprise grinding the zinc ferrite catalyst obtained in Step (B) before Step (C).

According to an exemplary embodiment of the present specification, in Step (C), the metal complex catalyst particles after the supporting of the acid onto the zinc ferrite catalyst can have a particle size of 0.6 mm to 0.85 mm.

According to an exemplary embodiment of the present specification, the method can further comprise calcining the zinc ferrite catalyst onto which phosphoric acid is supported, after Step (C). Specifically, the calcining of the zinc ferrite catalyst can be increasing the temperature up to 500° C. at a rate of 1° C./min, and then calcining the zinc ferrite catalyst for 6 hours.

According to an exemplary embodiment of the present specification, the method for preparing a metal complex catalyst can be a method for preparing a metal complex catalyst for an oxidative dehydrogenation reaction of butene.

An exemplary embodiment of the present specification provides a metal complex catalyst prepared by the above-described method for preparing a metal complex catalyst.

An exemplary embodiment of the present specification provides a method for preparing butadiene, the method comprising: preparing butadiene by using the metal complex catalyst, according to the above-described method for preparing a metal complex catalyst, in an oxidative dehydrogenation reaction of butene.

Another exemplary embodiment of the present specification provides a metal complex catalyst comprising a zinc ferrite catalyst and an acid.

According to an exemplary embodiment of the present specification, the acid can be phosphoric acid.

According to an exemplary embodiment of the present specification, the metal complex catalyst can be in the form in which an acid is supported onto a zinc ferrite catalyst.

According to an exemplary embodiment of the present specification, the metal complex catalyst can have a particle size of 0.6 mm to 0.85 mm.

According to an exemplary embodiment of the present specification, a metal complex catalyst comprising a zinc ferrite catalyst and an acid can be provided. Since phosphoric acid is not removed during the calcination, the amount of phosphoric acid initially introduced can remain as it is. Specifically, a content of the acid can be 0.05 wt % to 0.2 wt %, more specifically 0.05 wt % to 0.1 wt %, based on the total weight of the metal complex catalyst. In addition, a content of the zinc ferrite catalyst can be 99.8 wt % to 99.95 wt % based on the total weight of the metal complex catalyst.

When the content of the acid is less than 0.05 wt %, phosphoric acid is not sufficiently supported, so that the side reaction of the oxidative dehydrogenation reaction can not be sufficiently prevented, and when the content thereof is more than 0.2 wt %, the phosphoric acid is supported excessively to suppress the activity of the catalyst, so that the conversion of butene and the selectivity of butadiene can be reduced.

Further, an exemplary embodiment of the present specification provides a method for preparing butadiene, the method comprising: preparing butadiene by using the above-described metal complex catalyst in an oxidative dehydrogenation reaction of butene.

According to an exemplary embodiment of the present specification, the preparing of the butadiene can use a reactant comprising a C4 mixture. The C4 mixture comprises one or more normal butenes selected from 2-butene (trans-2-butene, cis-2-butene) and 1-butene as an example, and selectively, can further comprise normal butane or C4 raffinate-3. The reactant can further comprise one or more selected from air, nitrogen, steam, and carbon dioxide as an example, and preferably, further comprises nitrogen and steam. As a specific example, the reactant can comprise the C4 mixture, oxygen, steam, and nitrogen at a molar ratio of 1:0.1 to 1.5:1 to 15:0.5 to 10 or 1:0.5 to 1.2:5 to 12:0.5 to 5. Furthermore, the method for preparing butadiene according to an exemplary embodiment of the present specification has an advantage in that the reaction efficiency is excellent and waste water is generated in a small amount even though steam is used in a small amount of 1 to 10 or 5 to 10 mol based on 1 mol of the C4 mixture, and ultimately, provides an effect of reducing not only waste water treatment costs, but also energy consumed for the process. The oxidative dehydrogenation reaction can be performed at a reaction temperature of 250 to 500° C., 300° C. to 450° C., 320° C. to 400° C., 330° C. to 380° C., or 350° C. to 370° C. as an example, and within this range, the reaction efficiency is excellent without significantly increasing the energy costs, so that 1,3-butadiene can be provided with high productivity.

According to an exemplary embodiment of the present specification, the preparing of the butadiene can be performed under conditions of a reaction temperature of 360° C. and a gas hourly space velocity (GHSV) of 120 $h^{-1}$ in a single reactor, and the reactant can comprise the C4 mixture: oxygen:steam:nitrogen at a molar ratio of 1:0.67:5:2.67.

Further, according to an exemplary embodiment of the present specification, the preparing of the butadiene can be performed under conditions (of a reaction temperature of 360° C. and a gas hourly space velocity (GHSV) of 120 $h^{-1}$) in a two-stage reactor (a case where oxygen is not partitioned), and the reactant can comprise the C4 mixture: oxygen:steam:nitrogen at a molar ratio of 1:0.67:5:2.67.

FIG. 1 is an exemplary process diagram for performing a method for preparing a metal complex catalyst according to an exemplary embodiment of the present specification.

According to an exemplary embodiment of the present specification, in order to prevent a phenomenon in which the selectivity of butadiene of an α-iron oxide (α-$Fe_2O_3$) phase, which is formed when a catalyst for an oxidative dehydrogenation reaction of butene is prepared by the co-precipitation method, is reduced, it is possible to suppress a complete oxidation reaction, which is a side reaction of the oxidative dehydrogenation reaction of butene, by supporting phosphoric acid onto the prepared catalyst. Through this, it is possible to improve the reactivity of the zinc ferrite catalyst prepared by the co-precipitation method.

As described above, the metal complex catalyst according to an exemplary embodiment of the present specification can ultimately prepare butadiene with a high yield by increasing the conversion of butene and the selectivity of butadiene during the oxidative dehydrogenation reaction of butene.

EXEMPLARY EMBODIMENTS

Hereinafter, the present specification will be described in detail with reference to Examples for specifically describing the present specification. However, the Examples according to the present specification can be modified in various forms, and it is not interpreted that the scope of the present specification is limited to the Examples described below in detail. The Examples of the present specification are provided to more completely explain the present specification to a person with ordinary skill in the art.

Example 1

A metal precursor solution was prepared by dissolving 12.019 g of zinc chloride ($ZnCl_2$) and 37.662 g of ferric chloride ($FeCl_3$) in 404.59 g of distilled water. In this case, for a molar ratio of the metal components comprised in the metal precursor solution, Zn:F3 was 1:2. An aqueous ammonia solution was added dropwise to the prepared aqueous metal precursor solution such that the pH was 9, and the resulting solution was stirred for 1 hour and co-precipitated. Thereafter, a co-precipitate was obtained by filtering the co-precipitation solution under reduced pressure, and after the co-precipitate was dried at 90° C. for 16 hours, and then the temperature was increased up to 650° C. at a warming rate of 1° C./min at 80° C. under air atmosphere, a zinc-iron oxide ($ZnFe_2O_4$) powder having a spinel structure was prepared by maintaining the temperature for 6 hours. Phosphoric acid was supported in an amount of 0.05 wt %.

Example 2

A metal complex catalyst was prepared in the same manner as in Example 1, except that in Example 1, phosphoric acid was supported in an amount of 0.01 wt % instead of 0.05 wt %.

Example 3

A metal complex catalyst was prepared in the same manner as in Example 1, except that in Example 1, phosphoric acid was supported in an amount of 0.2 wt % instead of 0.05 wt %.

Comparative Example 1

A metal precursor solution was prepared by putting 20.865 g of $ZnCl_2$ and 81.909 g of $FeCl_3.6H_2O$ into 1,500 g of DI water and dissolving the resulting mixture. A catalyst precipitate was formed by putting 1,500 g of DI water into a reactor, simultaneously putting the metal precursor solution and 28 to 30 wt % of ammonia water into the reactor, and maintaining the pH at 8.

The formed precipitate was filtered by using a filter paper, and then dried in an oven at 90° C. Thereafter, the precipitate was warmed up to 650° C. at a rate of 1° C./min, and then calcined at 650° C. for 6 hours. In this case, the calcination was performed while air was injected at 1 L/min into a calcining furnace, thereby preparing a metal complex catalyst.

Comparative Example 2

A metal complex catalyst was prepared in the same manner as in Example 1, except that in Example 1, phosphoric acid was supported in an amount of 0.3 wt % instead of 0.05 wt %.

Comparative Example 3

A metal complex catalyst was prepared in the same manner as in Example 1, except that in Example 1, phosphoric acid was supported in an amount of 0.4 wt % instead of 0.05 wt %.

Comparative Example 4

A metal complex catalyst was prepared in the same manner as in Example 1, except that in Example 1, phosphoric acid was supported in an amount of 0.6 wt % instead of 0.05 wt %.

Comparative Example 5

After a manganese ferrite catalyst ($MnFe_2O_4$) was ground, the catalyst was warmed up to 500° C. at a rate of 1° C./min, and then calcined at 500° C. for 6 hours, thereby preparing a metal complex catalyst.

Experimental Example 1-1

An oxidative dehydrogenation reaction of butene was performed under conditions of a 2-butene reactant with the composition of 40 wt % of cis-2-butene and 60 wt % of trans-2-butene, 0.1 g of the metal complex catalyst prepared in Example 1, GHSV=262 $h^{-1}$, OBR=1, SBR=5, NBR=4, and a reaction temperature of 380° C., thereby preparing butadiene.

(GHSV=gas hourly space velocity, OBR=oxygen/total 2-butene ratio, SBR=steam/total 2-butene ratio, NBR=nitrogen/total 2-butene ratio)

Experimental Example 1-2

Butadiene was prepared in the same manner as in Experimental Example 1-1, except that in Experimental Example 1-1, the reaction temperature was 400° C. instead of 380° C.

Experimental Example 1-3

Butadiene was prepared in the same manner as in Experimental Example 1-1, except that in Experimental Example 1-1, the reaction temperature was 440° C. instead of 380° C.

Experimental Example 1-4

Butadiene was prepared in the same manner as in Experimental Example 1-1, except that in Experimental Example 1-1, the metal complex catalyst prepared in Example 2 was used instead of the metal complex catalyst prepared in Example 1.

Experimental Example 1-5

Butadiene was prepared in the same manner as in Experimental Example 1-4, except that in Experimental Example 1-4, the reaction temperature was 400° C. instead of 380° C.

Experimental Example 1-6

Butadiene was prepared in the same manner as in Experimental Example 1-4, except that in Experimental Example 1-4, the reaction temperature was 440° C. instead of 380° C.

Experimental Example 1-7

Butadiene was prepared in the same manner as in Experimental Example 1-1, except that in Experimental Example 1-1, the metal complex catalyst prepared in Example 3 was used instead of the metal complex catalyst prepared in Example 1.

Experimental Example 1-8

Butadiene was prepared in the same manner as in Experimental Example 1-4, except that in Experimental Example 1-7, the reaction temperature was 400° C. instead of 380° C.

Experimental Example 1-9

Butadiene was prepared in the same manner as in Experimental Example 1-4, except that in Experimental Example 1-7, the reaction temperature was 440° C. instead of 380° C.

Comparative Example 1-1

Butadiene was prepared in the same manner as in Experimental Example 1-1, except that in Experimental Example 1-1, the metal complex catalyst prepared in Comparative Example 1 was used instead of the metal complex catalyst prepared in Example 1.

Comparative Example 1-2

Butadiene was prepared in the same manner as in Comparative Example 1-1, except that in Comparative Example 1-1, the reaction temperature was 400° C. instead of 380° C.

Comparative Example 1-3

Butadiene was prepared in the same manner as in Comparative Example 1-1, except that in Comparative Example 1-1, the reaction temperature was 440° C. instead of 380° C.

Comparative Example 1-4

Butadiene was prepared in the same manner as in Experimental Example 1-1, except that in Experimental Example 1-1, the metal complex catalyst prepared in Comparative Example 2 was used instead of the metal complex catalyst prepared in Example 1.

Comparative Example 1-5

Butadiene was prepared in the same manner as in Comparative Example 1-4, except that in Comparative Example 1-4, the reaction temperature was 400° C. instead of 380° C.

Comparative Example 1-6

Butadiene was prepared in the same manner as in Comparative Example 1-4, except that in Comparative Example 1-4, the reaction temperature was 440° C. instead of 380° C.

Comparative Example 1-7

Butadiene was prepared in the same manner as in Experimental Example 1-1, except that in Experimental Example 1-1, the metal complex catalyst prepared in Comparative Example 3 was used instead of the metal complex catalyst prepared in Example 1.

Comparative Example 1-8

Butadiene was prepared in the same manner as in Comparative Example 1-7, except that in Comparative Example 1-7, the reaction temperature was 400° C. instead of 380° C.

Comparative Example 1-9

Butadiene was prepared in the same manner as in Comparative Example 1-7, except that in Comparative Example 1-7, the reaction temperature was 440° C. instead of 380° C.

Comparative Example 1-10

Butadiene was prepared in the same manner as in Experimental Example 1-1, except that in Experimental Example 1-1, the metal complex catalyst prepared in Comparative Example 4 was used instead of the metal complex catalyst prepared in Example 1.

Comparative Example 1-11

Butadiene was prepared in the same manner as in Comparative Example 1-10, except that in Comparative Example 1-10, the reaction temperature was 400° C. instead of 380° C.

Comparative Example 1-12

Butadiene was prepared in the same manner as in Comparative Example 1-10, except that in Comparative Example 1-10, the reaction temperature was 440° C. instead of 380° C.

Comparative Example 1-13

Butadiene was prepared in the same manner as in Experimental Example 1-1, except that in Experimental Example 1-1, the metal complex catalyst prepared in Comparative Example 5 was used instead of the metal complex catalyst prepared in Example 1.

Comparative Example 1-14

Butadiene was prepared in the same manner as in Comparative Example 1-13, except that in Comparative Example 1-13, the reaction temperature was 400° C. instead of 380° C.

Comparative Example 1-15

Butadiene was prepared in the same manner as in Comparative Example 1-13, except that in Comparative Example 1-13, the reaction temperature was 440° C. instead of 380° C.

In the oxidative dehydrogenation reaction of butene in each of Experimental Examples 1-1 to 1-9 and Comparative Examples 1-1 to 1-15, the results of measuring the conversion of butene and the selectivity of butadiene were shown in the following Table 1.

TABLE 1

| Classification | Catalyst | Reaction temperature (° C.) | Conversion (%) of butene | Selectivity (%) of butadiene |
|---|---|---|---|---|
| Experimental Example 1-1 | Example 1 | 380 | 79.3 | 92.0 |
| Experimental Example 1-2 | Example 1 | 400 | 79.6 | 92.3 |
| Experimental Example 1-3 | Example 1 | 440 | 72.3 | 89.6 |
| Experimental Example 1-4 | Example 2 | 380 | 80.6 | 91.5 |
| Experimental Example 1-5 | Example 2 | 400 | 79.5 | 91.1 |
| Experimental Example 1-6 | Example 2 | 440 | 75.4 | 89.9 |
| Experimental Example 1-7 | Example 3 | 380 | 78.6 | 91.6 |
| Experimental Example 1-8 | Example 3 | 400 | 79.2 | 90.5 |
| Experimental Example 1-9 | Example 3 | 440 | 74.1 | 88.9 |
| Comparative Example 1-1 | Comparative Example 1 | 380 | 77.9 | 91.7 |
| Comparative Example 1-2 | Comparative Example 1 | 400 | 79.0 | 90.3 |
| Comparative Example 1-3 | Comparative Example 1 | 440 | 70.7 | 89.1 |
| Comparative Example 1-4 | Comparative Example 2 | 380 | 39.9 | 75.4 |
| Comparative Example 1-5 | Comparative Example 2 | 400 | 45.0 | 74.7 |
| Comparative Example 1-6 | Comparative Example 2 | 440 | 51.7 | 72.9 |
| Comparative Example 1-7 | Comparative Example 3 | 380 | 7.4 | 64.5 |
| Comparative Example 1-8 | Comparative Example 3 | 400 | 13.1 | 59.9 |
| Comparative Example 1-9 | Comparative Example 3 | 440 | 29.6 | 57.2 |
| Comparative Example 1-10 | Comparative Example 4 | 380 | 8.0 | 50.4 |
| Comparative Example 1-11 | Comparative Example 4 | 400 | 13.1 | 44.4 |
| Comparative Example 1-12 | Comparative Example 4 | 440 | 23.4 | 53.5 |
| Comparative Example 1-13 | Comparative Example 5 | 380 | 29.1 | 47.3 |
| Comparative Example 1-14 | Comparative Example 5 | 400 | 26.8 | 46.5 |
| Comparative Example 1-15 | Comparative Example 5 | 440 | 22.2 | 40.2 |

According to Table 1, the metal complex catalysts prepared according to Examples 1 to 3 can improve the conversion of butene and the selectivity of butadiene by supporting phosphoric acid onto a zinc ferrite catalyst formed by the existing co-precipitation method. This is because it is possible to suppress the complete oxidation reaction which is a side reaction of the oxidative dehydrogenation reaction of butene.

When Experimental Examples 1-1 to 1-9 are compared with Comparative Examples 1-1 to 1-3, it can be confirmed that Experimental Examples 1-1 to 1-9 in which the zinc ferrite catalyst onto which phosphoric acid is supported is used have the higher conversion of butene and the higher selectivity of butadiene, in the entire region of the reaction temperatures of 380° C., 400° C., and 440° C., than those in Comparative Examples 1-1 to 1-3 in which the oxidative dehydrogenation reaction is performed with the zinc ferrite catalyst formed by the existing co-precipitation method.

When Experimental Examples 1-1 to 1-9 are compared with Comparative Examples 1-4 to 1-12, it can be confirmed that Experimental Examples 1-1 to 1-9 in which 0.05 wt % to 0.2 wt % of phosphoric acid is supported onto the zinc ferrite catalyst have the higher conversion of butene and the higher selectivity of butadiene, in the entire region of the reaction temperatures of 380° C., 400° C., and 440° C., than those in Comparative Examples 1-4 to 1-12 in which 0.3 wt % or more of phosphoric acid is supported onto the zinc ferrite catalyst.

In particular, in Comparative Examples 1-7 to 1-12 in which 0.4 wt % or more of phosphoric acid is supported, it can be confirmed that the conversion of butene and the selectivity of butadiene are remarkably lowered.

When Experimental Examples 1-1 to 1-6 are compared with Comparative Examples 1-13 to 1-15, it can be confirmed that the conversion of butene and the selectivity of butadiene in Experimental Examples 1-1 to 1-6 in which phosphoric acid is supported onto the zinc ferrite catalyst are remarkably better than those in Comparative Examples 1-13 to 1-15 in which phosphoric acid is supported onto the manganese ferrite catalyst during the oxidative dehydrogenation reaction of butene.

Although the preferred exemplary embodiments of the present invention have been described above, the present invention is not limited thereto, and various modifications can be made and carried out within the scopes of the claims and the detailed description of the invention, and also fall within the scope of the invention.

The invention claimed is:

1. A method for preparing a metal complex catalyst, the method comprising:
   (A) obtaining a precipitate by bringing a metal precursor solution comprising a zinc (Zn) precursor, a ferrite (Fe) precursor, and water into contact with a basic aqueous solution;
   (B) obtaining a zinc ferrite catalyst by filtering and calcining the precipitate; and
   (C) supporting an acid onto the zinc ferrite catalyst, wherein a content of the acid is 0.05 wt % to 0.2 wt % based on 100 weight % of the zinc ferrite catalyst, and calcining the zinc ferrite catalyst onto which the acid is supported.

2. The method of claim 1, wherein in Step (A), a content of the zinc precursor is 0.1 wt % to 5 wt % based on 100 weight % of water of the metal precursor solution.

3. The method of claim 1, wherein in Step (A), a content of the ferrite precursor is 1 wt % to 10 wt % based on 100 weight % of water of the metal precursor solution.

4. The method of claim 1, wherein in Step (C), the acid is phosphoric acid.

5. The method of claim 1, wherein the zinc precursor and the ferrite precursor are each independently one or more selected from the group consisting of: a nitrate, an ammonium salt, a sulfate, and a chloride, and a hydrate thereof.

6. The method of claim 1, wherein the zinc precursor is zinc chloride ($ZnCl_2$).

7. The method of claim 1, wherein the ferrite precursor is ferric chloride hydrate ($FeCl_3 \cdot 6H_2O$).

8. The method of claim 1, wherein a pH of the basic aqueous solution is 7 to 11.

9. The method of claim 1, wherein the basic aqueous solution is one or more selected from the group consisting of: potassium hydroxide, ammonium carbonate, ammonium bicarbonate, an aqueous sodium hydroxide solution, an aqueous sodium carbonate solution, and ammonium water.

10. The method of claim 1, further comprising:
    drying the precipitate before the precipitate is filtered and then calcined in Step (B).

11. A method for preparing butadiene, the method comprising:

preparing butadiene by using the metal complex catalyst prepared according to the method of claim 1 in an oxidative dehydrogenation reaction of butene.

12. A metal complex catalyst comprising a zinc ferrite catalyst and an acid, wherein the acid is present in an amount of 0.05 wt % to 0.2 wt % based on 100 weight % of the zinc ferrite catalyst.

* * * * *